United States Patent
Palero et al.

(10) Patent No.: US 12,076,578 B2
(45) Date of Patent: Sep. 3, 2024

(54) HAND-HELD DEVICE FOR PERFORMING A TREATMENT OPERATION

(71) Applicant: KONINKLIJKE PHILIPS N.V., Eindhoven (NL)

(72) Inventors: Jonathan Alambra Palero, Waalre (NL); Frank Anton Van Abeelen, Eindhoven (NL); Bastiaan Wilhelmus Maria Moeskops, Uden (NL); Yannyk Parulian Julian Bourquin, Eindhoven (NL); Kiran Kumar Thumma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 416 days.

(21) Appl. No.: 17/263,171

(22) PCT Filed: Aug. 9, 2019

(86) PCT No.: PCT/EP2019/071406
§ 371 (c)(1),
(2) Date: Jan. 26, 2021

(87) PCT Pub. No.: WO2020/035405
PCT Pub. Date: Feb. 20, 2020

(65) Prior Publication Data
US 2021/0178182 A1    Jun. 17, 2021

(30) Foreign Application Priority Data
Aug. 13, 2018 (EP) .................................... 18188712

(51) Int. Cl.
*A61N 5/06* (2006.01)
*A61N 5/00* (2006.01)

(52) U.S. Cl.
CPC ...... *A61N 5/0617* (2013.01); *A61N 2005/005* (2013.01); *A61N 2005/063* (2013.01); *A61N 2005/0644* (2013.01)

(58) Field of Classification Search
CPC .. A61N 2005/0644; A61N 5/06; A61N 5/016; A61N 5/017; A61B 18/203
See application file for complete search history.

(56) References Cited

U.S. PATENT DOCUMENTS

2005/0197681 A1*  9/2005  Barolet ................ A61N 5/0616
                                                            607/86
2006/0247740 A1   11/2006  Roersma
(Continued)

FOREIGN PATENT DOCUMENTS

DE      102004063370      8/2005
JP        2006000543      1/2006
(Continued)

OTHER PUBLICATIONS

International Search Report and Written Opinion Dated Oct. 11, 2019 for International Application No. PCT/EP2019/071406 Filed Aug. 9, 2019.

*Primary Examiner* — Yingchuan Zhang
*Assistant Examiner* — Jessica L Mullins (57) ABSTRACT

According to an aspect, there is provided a hand-held skin treatment device (2) for applying light to skin of a subject to perform a treatment operation. The hand-held device (2) comprises a rigid main housing (4) accommodating a cooling unit (19); a first treatment head portion (12) coupled to the main housing (4) for performing the treatment operation on a first skin portion, wherein the first treatment head portion (12) comprises a first optical waveguide (16) having a first skin-contact surface (17) with a first total surface area, a first light source (14) for generating light and applying the (Continued)

light to the first skin portion via the first optical waveguide (16) and the first skin-contact surface (17), and a first heat sink (18) thermally coupled to the first light source (14) and to the cooling unit (19); a second treatment head portion (20) for performing the treatment operation on a second skin portion adjacent to the first skin portion, wherein the second treatment head portion (20) comprises a second optical waveguide (24) having a second skin-contact surface (25) with a second total surface area, a second light source (22) for generating light and applying the light to the second skin portion via the second optical waveguide (24) and the second skin-contact surface (25), and a second heat sink (26) thermally coupled to the second light source (22); wherein the hand-held device (2) is operable in (i) a first configuration in which the first and second treatment head portions (12; 20) are in a first spatial arrangement relative to the main housing (4) such that, in an operational position of the main housing (4) relative to the skin, only the first skin-contact surface (17) is arranged in a treatment position relative to the main housing (4) such as to be able to contact the skin over the first total surface area; and (ii) a second configuration in which the second treatment head portion (20) is coupled to the main housing (4) and the second heat sink (26) is thermally coupled to the cooling unit (19), and in which the first and second treatment head portions (12; 20) are in a second spatial arrangement relative to the main housing (4), different from the first spatial arrangement, such that, in the operational position of the main housing (4), the first skin-contact surface (17) and the second skin-contact surface (25) are each arranged in a treatment position relative to the main housing (4) such as to be able to contact the skin over, respectively, the first total surface area and the second total surface area.

20 Claims, 6 Drawing Sheets

(56) References Cited

U.S. PATENT DOCUMENTS

| | | |
|---|---|---|
| 2007/0038206 A1 | 2/2007 | Altshuler |
| 2007/0049910 A1 | 3/2007 | Altshuler |
| 2007/0255265 A1 | 11/2007 | Davenport |
| 2008/0058783 A1 | 3/2008 | Altshuler |
| 2009/0210037 A1 | 8/2009 | Roersma |
| 2009/0234342 A1 * | 9/2009 | Ely ................. A61B 18/203 606/9 |
| 2011/0004201 A1 | 1/2011 | Nuijs |
| 2013/0344454 A1 | 12/2013 | Nath |
| 2015/0306419 A1 | 10/2015 | Domankevitz |

FOREIGN PATENT DOCUMENTS

| | | | |
|---|---|---|---|
| WO | 2013/011505 | 1/2013 | |
| WO | WO-2018208066 A1 * | 11/2018 | ............ A61N 5/00 |

* cited by examiner

HAND-HELD DEVICE FOR PERFORMING A TREATMENT OPERATION

CROSS REFERENCE TO RELATED APPLICATIONS

This application is the U.S. National Phase application under 35 U.S.C. § 371 of International Application No. PCT/EP2019/071406 filed Aug. 9, 2019, which claims the benefit of European Patent Application Number 18188712.6 filed Aug. 13, 2018. These applications are hereby incorporated by reference herein.

FIELD OF THE INVENTION

This disclosure relates to a hand-held device for performing a treatment operation on skin of a subject, and in particular to a treatment operation in which light is applied to the skin.

BACKGROUND OF THE INVENTION

Techniques for removal of unwanted hairs include shaving, electrolysis, plucking, laser and light therapies (known as photoepilation) and injection of therapeutic anti-androgens. Light-based technologies are also used in other types of dermatological treatments, including hair growth reduction and treating acne.

Through the use of an appropriate configuration of the light energy, i.e. in terms of wavelength, intensity and/or pulse duration (if the light is to be pulsed), selective heating of the hair root and subsequent temporary or permanent damage to the hair follicle can be achieved.

Home-use photoepilation devices, for example the Philips Lumea device, use intense pulsed light (IPL) from high intensity light sources, e.g. Xenon flash lamps that produce high output bursts of broad spectrum light. In these devices, the light (IPL) is coupled to the skin via air.

A drawback of photoepilation devices based on gas discharge lamps is that a large part of the emitted energy is located in the visible part of the spectrum. A light shield is required to prevent disturbing and potentially harmful stray light. This shield reduces the user's view of the skin being treated. Furthermore, proper contact between the skin and shield has to be ensured. Typically, sensors, such as skin contact sensors, verify this. While treating more angular and bony areas of the body (e.g. around the knee) a gap between the treatment head of the photoepilation device and the skin can easily occur. In this case, the sensors may prevent flashing because of improper shielding.

The narrow bandwidth of light emitting diodes (LEDs) may bring therapeutic advantages to light-based skin treatment devices. However, in a light-based skin treatment device (particularly photoepilators), the LED emittance is highly limiting and the angular distribution of the emitted light is wide (approximately Lambertian), and so optical coupling to the skin via air is not efficient, and is not a preferred option. For Lambertian emission, the flux that can be transported through a given surface area is proportional to $n^2$, where n is the refractive index of the medium. Furthermore, both the source (n>3) and the target skin (n≈1.5) have a refractive index that is significantly higher than air. Consequently, an air layer forms a barrier for light transport from the LED(s) to the skin. Therefore a light waveguide (typically with refractive index ≥1.5) is used. This light waveguide is optically coupled to the LED(s) and provides optical contact with the skin when the waveguide is applied to it (often with slight pressure).

SUMMARY OF THE INVENTION

However, providing a non-air optical coupling presents a new challenge for photoepilators and other light-based skin treatment devices, since they are ideally used for different body regions that usually require different treatment head sizes, such as the legs, arms, armpits, face, upper lip area, etc. Conventional devices can be provided with exchangeable treatment head attachments having different sizes for different body regions. There is no issue with this in the case of optical coupling via air. In the case of non-air optical coupling, these attachments mainly comprise a window or a light waveguide that needs to be optically coupled to the light source in a detachable way. However, it is difficult to achieve and maintain a good optical coupling after several detachments and attachments with acceptable reliability.

An alternative approach is to integrate differently dimensioned light source arrays into the different attachments to circumvent the problem of optical coupling, but this makes the attachments expensive, since the light source arrays tend to be the most expensive elements of the device.

Therefore, there is a need for an alternative approach to provide a device for performing a treatment operation that can be adapted to treat different sized areas.

According to a first specific aspect, there is provided a hand-held skin treatment device for applying light to skin of a subject to perform a treatment operation, the hand-held device comprising a rigid main housing accommodating a cooling unit; a first treatment head portion coupled to the main housing for performing the treatment operation on a first skin portion, wherein the first treatment head portion comprises a first optical waveguide having a first skin-contact surface with a first total surface area, a first light source for generating light and applying the light to the first skin portion via the first optical waveguide and the first skin-contact surface, and a first heat sink thermally coupled to the first light source and to the cooling unit; a second treatment head portion for performing the treatment operation on a second skin portion adjacent to the first skin portion, wherein the second treatment head portion comprises a second optical waveguide having a second skin-contact surface with a second total surface area, a second light source for generating light and applying the light to the second skin portion via the second optical waveguide and the second skin-contact surface, and a second heat sink thermally coupled to the second light source; wherein the hand-held device is operable in (i) a first configuration in which the first and second treatment head portions are in a first spatial arrangement relative to the main housing such that, in an operational position of the main housing relative to the skin, only the first skin-contact surface is arranged in a treatment position relative to the main housing such as to be able to contact the skin over the first total surface area; and (ii) a second configuration in which the second treatment head portion is coupled to the main housing and the second heat sink is thermally coupled to the cooling unit, and in which the first and second treatment head portions are in a second spatial arrangement relative to the main housing, different from the first spatial arrangement, such that, in the operational position of the main housing, the first skin-contact surface and the second skin-contact surface are each arranged in a treatment position relative to the main housing such as to be able to contact the skin over, respectively, the first total surface area and the second total surface area.

This and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

As noted above, it is desirable to provide a hand-held device for performing a treatment operation in which light is applied to the skin of a subject that can be adapted to treat different sized areas, such as the legs, arms, armpits, face, upper lip area, etc. As described herein, a hand-held device is operated or used by a 'user', and the treatment operation is performed on a 'subject'. In some cases the user and the subject is the same person, i.e. the hand-held device is held in a hand and used by a user on themselves (e.g. for treating the skin on their leg). In other cases the user and the subject are different people, e.g. the hand-held device is held in a hand and used by a user on someone else. The treatment operation can be any type of treatment operation that is typically performed using light, including light pulses. For example, the treatment operation can be hair removal, hair reduction, photoepilation, treatment of skin conditions such as psoriasis, eczema or acne, phototherapy treatment, photodynamics therapy (the local photosensitizing of a drug by light) or pain relief.

Generally, the invention provides that a hand-held device comprises a first treatment head portion for performing the treatment operation on the skin of the subject, with the first treatment head portion comprising a first optical waveguide having a first skin-contact surface (that is for contacting the skin) and a first light source for generating light and applying the light to the skin via the first optical waveguide and the first skin-contact surface. The first skin-contact surface has a surface area that is referred to herein as a 'first total surface area', and the area of skin treated by the light applied via the first optical waveguide and the first skin-contact surface is referred to herein as a 'first skin portion'. The hand-held device can include a main housing, for example a rigid main housing (i.e. that is not deformable or is substantially not deformable). The first treatment head portion can be coupled to the main housing. The hand-held device also includes a second treatment head portion for performing the treatment operation on the skin of the subject (and in particular on a 'second skin portion' that is adjacent to the first skin portion), with the second treatment head portion comprising a second optical waveguide that has a second skin-contact surface (that has a surface area referred to as a 'second total surface area'), a second light source for generating light and applying the light to the skin via the second optical waveguide and the second skin-contact surface. The hand-held device is operable in one of two configurations. In a first configuration, only the first treatment head portion is operable to perform the treatment operation on the skin, and results in the first skin portion of the skin of the subject being treated. In the first configuration, the second treatment head portion is not able to perform the treatment operation and the second optical waveguide is not able to contact the skin. Thus, in the first configuration, the first and second treatment head portions can be in a first spatial arrangement relative to the main housing of the hand-held device such that, in an operational position of the main housing relative to the skin, only the first skin-contact surface is arranged in a treatment position relative to the main housing so as to be able to contact the skin over the first total surface area. In a second configuration, both the first treatment head portion and the second treatment head portion are operable to perform the treatment operation on the skin, resulting in a larger area of the skin being treated than in the first configuration. Thus, in the second configuration, the second treatment head portion is coupled to the main housing, and the first and second treatment head portions are in a second spatial arrangement relative to the main housing, different from the first spatial arrangement, such that, in the operational position of the main housing, the first skin-contact surface and the second skin-contact surface are each arranged in a treatment position relative to the main housing so as to be able to contact the skin over, respectively, the first total surface area and the second total surface area.

As described in more detail below, the first configuration may be enabled by removing or detaching the second treatment head portion from the hand-held device, retracting the second treatment head portion in the hand-held device with respect to the first treatment head portion, or extending the first treatment head portion in the hand-held device with respect to the second treatment head portion. The second configuration may be enabled by attaching the second treatment head portion to the hand-held device, retracting the first treatment head portion in the hand-held device with respect to the second treatment head portion (so that the optical waveguides and skin-contact surfaces of the treatment head portions are aligned), or extending the second treatment head portion in the hand-held device with respect to the first treatment head portion (so that the optical waveguides and skin-contact surfaces of the treatment head portions are aligned).

This arrangement of the hand-held device enables different sized areas of skin to be treated as required by the user (e.g. using the first configuration to treat an armpit, and using the second configuration to treat a leg). In addition, as in the second configuration the treatment head portions are used together, it is possible to treat different sized areas of skin without having to provide completely interchangeable treatment heads (i.e. with a larger light source/light source array for treating a larger area of skin and a smaller light source/light source array for treating a smaller area of skin), thereby reducing the cost associated with manufacturing such a device. In addition, each of the treatment head portions has a respective optical waveguide for contacting the skin and a respective light source for generating light, and the light sources/optical waveguides are used alongside each other, so this reduces problems associated with having to couple optical waveguides to light sources when changing treatment head portions.

In generating light, particularly (but not exclusively) light pulses, the light sources may get hot and require cooling in order to avoid damaging the hand-held device, to avoid a (substantial) drop in light output of LEDs (since light output depends on the temperature of the junction) and/or to avoid burning the skin. As such, each of the first treatment head portion and the second treatment head portion can include a respective heat sink that is thermally coupled to the respective light source. In this way, the heat sink can draw heat away from the light source, reducing the temperature increase of the light source following the generation of light or a light pulse. The hand-held device also includes a cooling unit, such as a fan, located in the main housing of the device, and the heat sinks in the first and second treatment head portions can be thermally coupled to the cooling unit to enable heat to be drawn out of the respective treatment head portion and removed from the device. Thus, in the first configuration, the heat sink in the first treatment head portion is thermally coupled to the cooling unit to cool the first light source, and in the second configuration, the heat sink in the first treatment head portion is thermally coupled to the cooling unit to cool the first light source, and the heat sink in the second treatment head portion is also thermally coupled to the cooling unit to cool the second light source.

Figure 1:
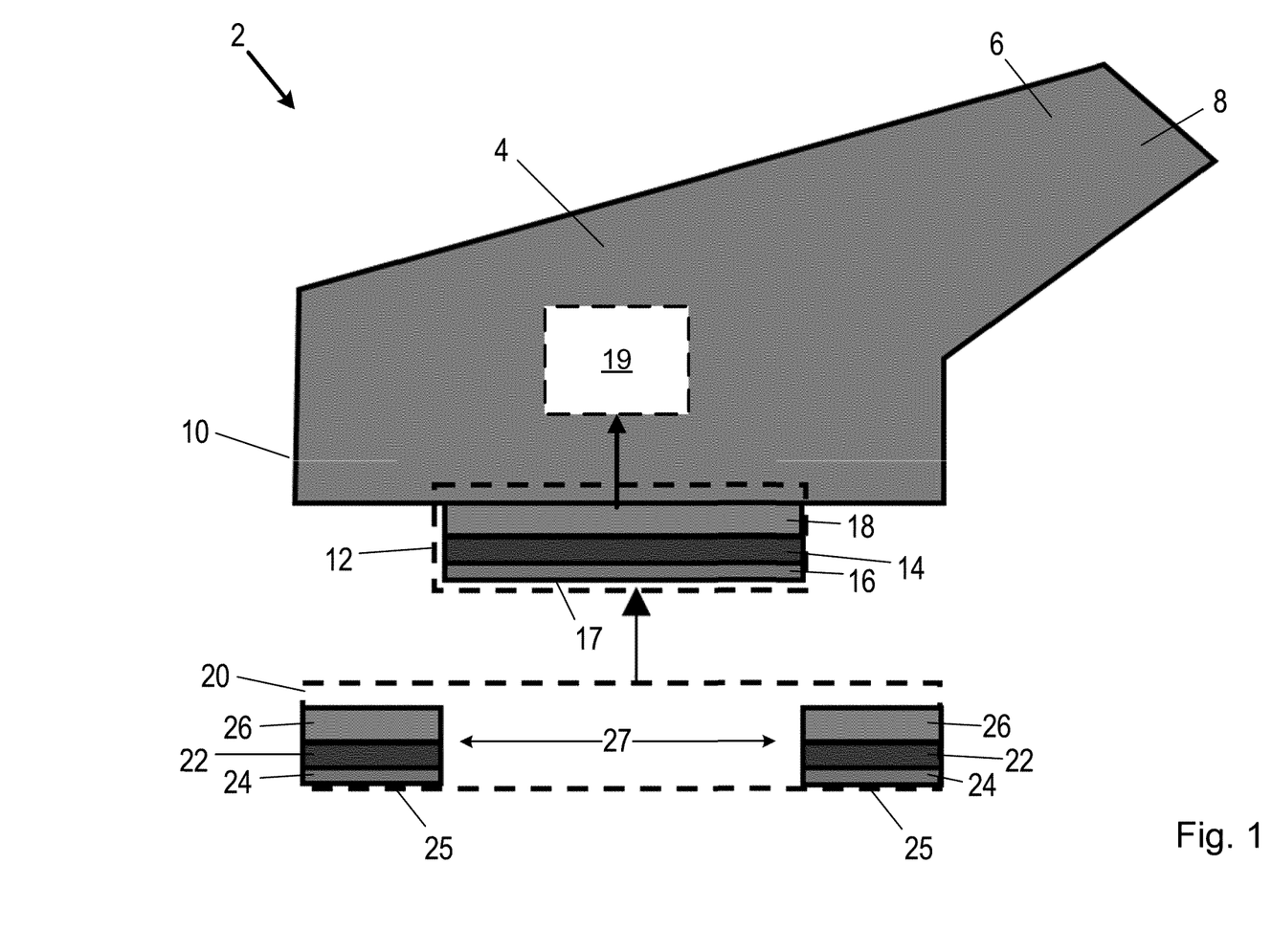
FIG. 1 is a simplified cross-section through an exemplary hand-held device according to an embodiment.

FIG. 1 is a simplified cross-section through an exemplary hand-held device 2 according to an embodiment. The hand-held device 2 comprises a main housing 4 that is shaped and/or sized or otherwise configured to be held in a hand of a user so that the user can place a part of the hand-held device 2 in contact with the skin of a subject (i.e. the person or animal that the treatment operation is to be performed on). As such, the hand-held device 2/main housing 4 may include a handle portion 6 located at a first end 8 of the hand-held device 2/main housing 4. The opposite end of the hand-held device 2/main housing 4 is referred to as the treatment end 10. The main housing 4 is preferably rigid, which means that it is not deformable, or it is substantially non-deformable.

The hand-held device 2 includes a first treatment head portion 12 at the treatment end 10. The first treatment head portion 12 is coupled (e.g. fixed) to the main housing 4. For example the first treatment head portion 12 can be attached to, be part of, or be integral with the main housing 4. The first treatment head portion 12 is for performing a treatment operation (e.g. photoepilation) on a part of the skin of the subject. The part of the skin that the first treatment head portion 12 performs the treatment operation on is referred to as a first skin portion.

The first treatment head portion 12 includes a first light source 14 that is for generating light. In some embodiments, the first light source 14 is used to generate pulses of light, but in other embodiments the first light source 14 can be used to continuously generate light. The first treatment head portion 12 also includes a first optical waveguide 16 that is for contacting the skin of the subject and that is arranged in the first treatment head portion 12 so that the light generated by the first light source 14 passes through the first optical waveguide 16 to the skin via a first skin-contact surface 17 of the first optical waveguide 16. The first optical waveguide 16, and particularly the first skin-contact surface 17 (which is for contacting the skin of the subject) defines the first skin portion. The first skin-contact surface 17 has a first total surface area. The first treatment head portion 12 also includes a first heat sink 18 that is thermally coupled to the first light source 14 so that heat is drawn out of or away from the first light source 14. An exemplary embodiment of the first heat sink 18 is a body made of a metal with a high thermal conductivity, like copper. This metal body can be thermally coupled to a part of the first light source 14 (e.g. a substrate of an LED where the first light source 14 is, or includes, one or more LEDs) via thermally conductive paste or a liquid metal compound. A substrate can commonly be made of a ceramic material with high thermal conductivity combined with good electrical isolation, like aluminium nitride (AlN).

The first light source 14 can be configured to generate light or a light pulse at any suitable or desired wavelength (or range of wavelengths) and/or intensities. For example, the first light source 14 can generate visible light, infra-red (IR) light and/or ultraviolet (UV) light. The first light source 14 can include one or more light sources, for example with the one or more light sources arranged in an array, and each light source can comprise any suitable type of light source, such as one or more light emitting diodes (LEDs), a laser or lasers, etc. In a preferred embodiment, the hand-held device 2 is for performing photoepilation, and the first light source 14 is to provide intense light pulses.

Where light pulses are used, the light pulses are pulses of light at a high intensity for a short duration (e.g. less than 1 second). The intensity of the light pulse should be high enough to effect the treatment operation on the skin in the first skin portion.

Although not shown in FIG. 1, the first treatment head portion 12 or the main housing 4 can include suitable driving circuitry and/or components (including a power source) for causing the first light source 14 to generate the light or light pulses in response to a trigger signal. The trigger signal can, for example, be provided in response to the user pressing or operating an actuation control on the main housing 4 (not shown in FIG. 1), such as a switch, trigger, or button.

The first heat sink 18 is thermally coupled to a cooling unit 19 in the main housing 4. The cooling unit 19 operates to cool the first heat sink 18. The cooling unit 19 can cool the first heat sink 18 by passing air or another coolant (e.g. a liquid, such as water) over or around the first heat sink 18, or alternatively the first heat sink 18 can be thermally coupled to a heat sink in the cooling unit 19 so that heat is drawn out of the first heat sink 18 to the heat sink in the cooling unit 19. In the latter case, the cooling unit 19 can cool the cooling unit heat sink by passing air or another coolant (e.g. a liquid, such as water) over or around the heat sink. In some embodiments, the cooling unit 19 is or includes a fan.

The hand-held device 2 also includes a second treatment head portion 20. The second treatment head portion 20 is for performing a treatment operation (and in particular the same type of treatment operation as the first treatment head portion 12) on a part of the skin of the subject. The part of the skin that the second treatment head portion 20 performs the treatment operation on is referred to as a second skin portion.

In this illustrated embodiment, the second treatment head portion 20 can be selectively attached to the treatment end 10 of the main housing 4, depending on the size of the area of skin that is to be treated by the hand-held device 2. Thus the second treatment head portion 20 is detachable or removable from the main housing 4. FIG. 1 does not show an attachment mechanism for the second treatment head portion 20, but those skilled in the art will be aware of various types of attachment mechanism that can be used to detachably couple the second treatment head portion 20 to the main housing 4, and that can enable a user to readily remove the second treatment head portion 20 as required.

The second treatment head portion 20 includes a second light source 22 that is for generating light. In some embodiments, the second light source 22 is used to generate pulses of light, but in other embodiments the second light source 22 can be used to continuously generate light. The second treatment head portion 20 also includes a second optical waveguide 24 that is for contacting the skin of the subject and that is arranged in the second treatment head portion 20 so that the light generated by the second light source 22 passes through the second optical waveguide 24 to the skin via a second skin-contact surface 25 of the second optical waveguide 24. The second optical waveguide 24, and particularly the second skin-contact surface 25 (which is for contacting the skin of the subject) defines the second skin portion. The second skin-contact surface 25 has a second total surface area (which can be smaller, larger, or the same size as the first total surface area). The second treatment head portion 20 also includes a second heat sink 26 that is thermally coupled to the second light source 22 so that heat is drawn out of or away from the second light source 22. The second heat sink 26 can be in a similar form to the first heat sink 18 described above.

Similar to the first light source 14, the second light source 22 can be configured to generate light or a light pulse at any suitable or desired wavelength (or range of wavelengths) and/or intensities. Preferably, the second light source 22 is configured to generate light or light pulses at the same wavelength (or range of wavelengths) and/or intensities as the first light source 14. Thus, for example, the second light source 22 can generate visible light, infra-red (IR) light and/or ultraviolet (UV) light. Similar to the first light source 14, the second light source 22 can include one or more light sources, for example with the one or more light sources arranged in an array, and each light source can comprise any suitable type of light source, such as one or more light emitting diodes (LEDs), a laser or lasers, etc. In the preferred embodiment, the hand-held device 2 is for performing photoepilation, and the second light source 22 is to provide intense light pulses.

Where light pulses are used, the light pulses are pulses of light at a high intensity for a short duration (e.g. less than 1 second). The intensity of the light pulse should be high enough to effect the treatment operation on the skin in the second skin portion.

Although not shown in FIG. 1, in some embodiments, the second treatment head portion 20 can include suitable driving circuitry and/or components (including a power source) for causing the second light source 22 to generate the light pulses in response to a trigger signal (that is provided by the same actuation control as used for the first treatment head portion 12). Alternatively, the second treatment head portion 20 can connect to suitable driving circuitry and/or components (including the power source) in the main housing 4. This driving circuitry and/or components may, for example, be shared by or with the first treatment head portion 12.

When the second treatment head portion 20 is detached or removed from the main housing 4, the hand-held device 2 operates in a first configuration with just the first treatment head portion 12. That is, the hand-held device 2 operates to perform the treatment operation on the first skin portion.

In this first configuration, the first treatment head portion 12 and the second treatment head portion 20 are considered to be in a first spatial arrangement relative to the main housing 4. That is, the first treatment head portion 12 is attached to or part of the main housing 4, and the second treatment head portion 20 is spaced/separated from the main housing 4. This first spatial arrangement means that, when the main housing 4 is in an operational position relative to the skin (i.e. where the main housing 4 is being held so that a treatment operation can be performed), only the first skin-contact surface 17 is arranged in a treatment position relative to the main housing 4 so that the first skin-contact surface 17 contacts the skin over the first total surface area.

When the second treatment head portion 20 is attached to the main housing 4, the hand-held device 2 operates in a second configuration and uses both the first treatment head portion 12 and the second treatment head portion 20 to perform the treatment operation on skin of the subject.

In this second configuration, the first treatment head portion 12 and the second treatment head portion 20 are considered to be in a second spatial arrangement relative to the main housing 4 (different to the first spatial arrangement). That is, the first treatment head portion 12 is attached to or part of the main housing 4, and the second treatment head portion 20 is also attached to the main housing 4 or attached to the first treatment head portion 12. This second spatial arrangement means that, when the main housing 4 is in an operational position relative to the skin (i.e. where the main housing 4 is being held so that a treatment operation can be performed), the first skin-contact surface 17 and the second skin-contact surface 25 are each arranged in a treatment position relative to the main housing 4 so that they are able to contact the skin over, respectively, the first total surface area and the second total surface area.

Thus, the second treatment head portion 20 can be attached or coupled to the main housing 4 such that the first skin portion treated by the first treatment head portion 12 and the second skin portion treated by the second treatment head portion 20 are adjacent to each other, so as to form an overall portion of skin that is to be treated when the main housing 4 is in the operational position. In particular, when the second treatment head portion 20 is attached to the main housing 4, the second skin-contact surface 25 of the second optical waveguide 24 can be adjacent to, and in the same plane as, the first skin-contact surface 17 of the first optical waveguide 16 in the first treatment head portion 12.

In addition, when the second treatment head portion 20 is attached or coupled to the main housing 4 or the first treatment head portion 12 in the second spatial arrangement, the second heat sink 26 thermally couples to the cooling unit 19 in the main housing 4. Similar to the first heat sink 18, the cooling unit 19 in the main housing 4 operates to cool the second heat sink 26, and can operate as described above.

In the illustrated embodiment, the second light source 22, the second optical waveguide 24 and the second heat sink 26 are effectively split into two parts 27 that are arranged so that they are either side of the first light source 14, the first optical waveguide 16 and the first heat sink 18 in the first treatment head portion 12 when the second treatment head portion 20 is attached to the main housing 4. In this way, the size of the skin portion that is treated in the first configuration is extended laterally by the attachment of the second treatment head portion 20 to the main housing 4. Thus, although the second treatment head portion 20 is described above as comprising a second light source 22, a second optical waveguide 24 and a second heat sink 26, each part 27 can be understood as comprising a respective second light source 22, a respective second optical waveguide 24 and a respective second heat sink 26.

Figure 2:
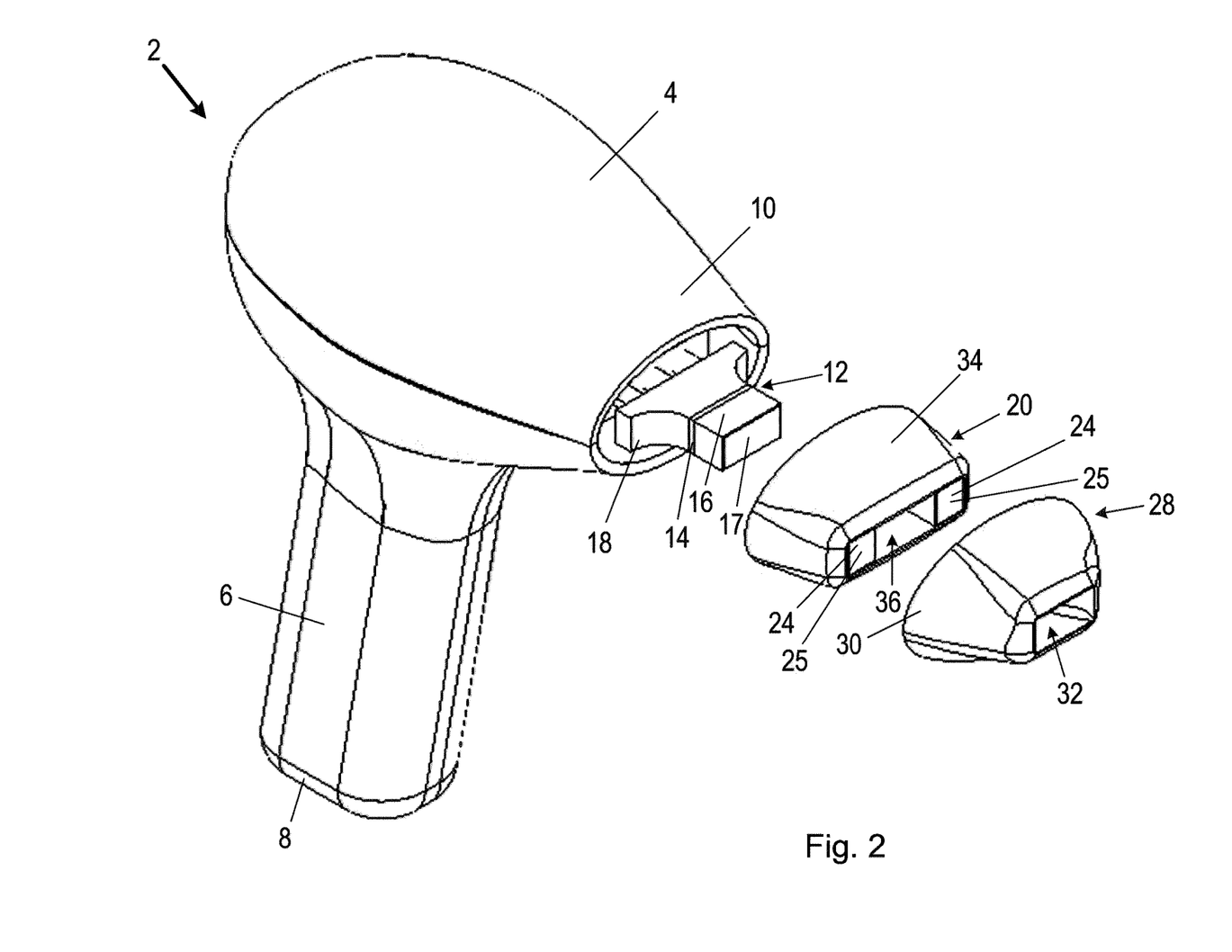
FIG. 2 is a perspective view of another exemplary hand-held device according to an embodiment.
Figure 3:
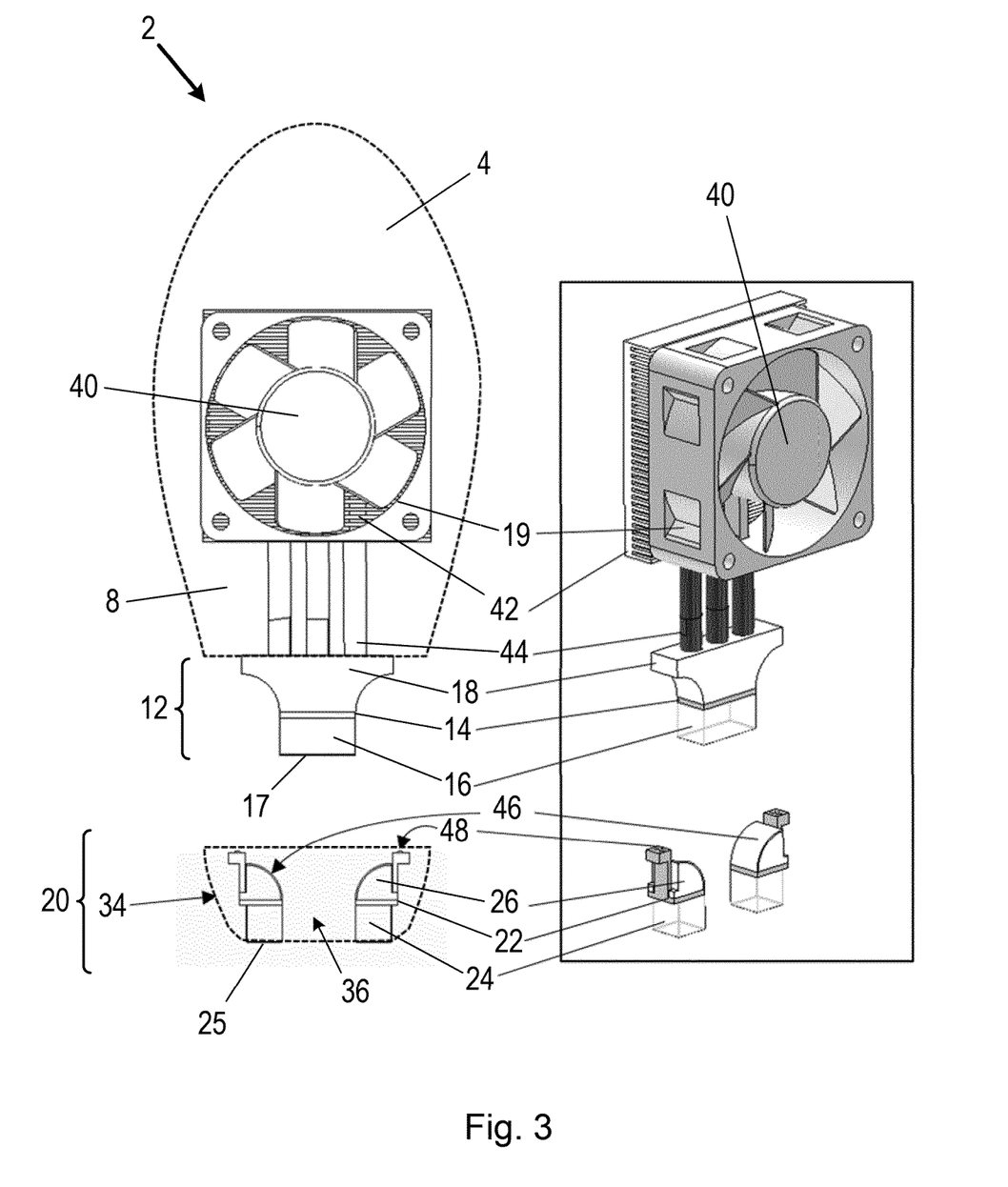
FIG. 3 is a cut-away view showing exemplary components of the exemplary hand-held device shown in FIG. 2.

FIGS. 2 and 3 show another exemplary hand-held device according to an embodiment. In particular, FIG. 2 is a perspective view of a hand-held device, and FIG. 3 shows a cut-away view of the top of the hand-held device. In FIGS. 2 and 3, components, features or elements of the hand-held device that are common to the embodiment shown in FIG. 1 use the same reference numerals, and, unless otherwise indicated below, these components, features and elements are as described above with respect to FIG. 1.

In the embodiment of FIGS. 2 and 3, the second treatment head portion 20 is removable or detachable from the main housing 4, as described above for the embodiment in FIG. 1. In the embodiment in FIGS. 2 and 3, when the second treatment head portion 20 is attached to the main housing 4 in the second configuration, the first treatment head portion 12 and the second treatment head portion 20 are such that the second heat sink 26 is in contact with the first heat sink 18, so that heat from the second light source 22 is conveyed to the cooling unit 19 via the second heat sink 26 and the first heat sink 18.

As such, when the second treatment head portion 20 is removed from the main housing 4, the first heat sink 18 and the other components of the first treatment head portion 12 (i.e. the first light source 14 and the first optical waveguide 16) may be exposed. Therefore the hand-held device 2 further comprises a treatment head protective cover 28 that can be removably attached to the main housing 4 when the hand-held device 2 is used in the first configuration. The treatment head protective cover 28 comprises a housing 30 that covers the first heat sink 18 and the first light source 14 so they are not exposed, and the housing 30 has an aperture 32 through which the first optical waveguide 16 projects when the protective cover 28 is coupled to the main housing 4, so that the first optical waveguide 16 is able to contact the skin of the subject. In some embodiments, the first skin-contact surface 17 of the first optical waveguide 16 is flush (i.e. level) with the housing 30 when the protective cover 28 is coupled to the main housing 4, but in other embodiments the first skin-contact surface 17 of the first optical waveguide 16 projects beyond the housing 30. This latter embodiment may make it easier for the user to see the skin portion to be treated.

Although not shown in FIG. 2, the treatment head protective cover 28 includes a suitable mechanism for enabling the treatment head protective cover to be removably coupled to the main housing 4 when the second treatment head portion 20 is not coupled to the main housing 4.

The second treatment head portion 20 includes a housing 34 that covers the components of the second treatment head portion 20 (i.e. the second light source 22, the second optical waveguide 24 and the second heat sink 26), and the housing 34 comprises an aperture 36 through which the first optical waveguide 16 projects when the second treatment head portion 20 is coupled to the main housing 4, so that the first optical waveguide 16 and the second optical waveguide 24 are adjacent to each other and provide a flat surface for contacting skin. In some embodiments, the first skin-contact surface 17 of the first optical waveguide 16 and the second skin-contact surface 25 of the second optical waveguide 24 are flush (i.e. level) with the housing 34 when the second treatment head portion 20 is coupled to the main housing 4, but in other embodiments the first skin-contact surface 17 of the first optical waveguide 16 and the second skin-contact surface 25 of the second optical waveguide 24 project beyond the housing 34. This latter embodiment may make it easier for the user to see the skin portion to be treated.

Referring now to FIG. 3, FIG. 3 shows a cooling unit 19 inside the main housing 4. In this illustrated embodiment, the cooling unit 19 includes a fan 40 and a heat sink 42 (referred to herein as a 'cooling unit' heat sink 42). The cooling unit heat sink 42 is coupled to the first heat sink 18 via a set of heat pipes 44. The set of heat pipes 44 can include one or more heat pipes 44, and three heat pipes 44 are shown in FIG. 3. The heat pipes 44 act to convey heat from the first heat sink 18 to the cooling unit heat sink 42. The fan 40 operates to pass air over the cooling unit heat sink 42 to cool the cooling unit heat sink 42 and thereby cool the hand-held device 2. Those skilled in the art will appreciate that alternative types of cooling unit 19 can be used, for example, Peltier elements between the cold end of the heat pipes 44 and the cooling unit heat sink 42 (a Peltier element can maintain a temperature difference, setting the cooling unit heat sink 42 at a higher temperature with respect to the ambient temperature, thus increasing its cooling capacity (albeit at the cost of extra generation in the Peltier)); a large cooling unit heat sink 42 without a fan (this would be a passive cooling solution); thermal coupling to the user's hand, effectively using the user's body as a heat sink; and/or a phase change material.

As noted above the first treatment head portion 12 and the second treatment head portion 20 are such that the second heat sink 26 is in contact with the first heat sink 18 when the second treatment head portion 20 is attached to the main housing 4. The first heat sink 18 and the second heat sink 26 can have any suitable shape or configuration to enable the contact therebetween. In the embodiment of FIGS. 2 and 3, the first heat sink 18 has two curved surfaces and the second heat sink 26 has two correspondingly curved surfaces to maximise the contact area between the first heat sink 18 and the second heat sink 26. Those skilled in the art will appreciate that other shapes and configurations are possible.

In some embodiments, the surface of the first heat sink 18 and/or the surface of the second heat sink 26 comprises a compressible thermal coupling or a heat transfer element 46, such as thermal gap fillers or pads. One exemplary type of thermal gap filler 46 that can be used is Tflex® HD90000 by Laird, although those skilled in the art will be aware of other types of thermal coupling or heat transfer elements that can be used.

In the embodiment of FIGS. 2 and 3, the power source for the first light source 14 and the second light source 22 is located in the main housing 4 (although not shown in FIGS. 2 and 3), and so the second light source 22 requires an electrical connection to the power source in the main housing 4 when the second treatment head portion 20 is coupled to the main housing 4. Therefore the second treatment head portion 20 comprises one or more electrical connectors 48 for connecting the second light source 22 to the power source. As such, the main housing 4 can include one or more corresponding electrical connectors (not shown in FIGS. 2 and 3) that contact the electrical connector(s) 48 when the second treatment head portion 20 is attached to the main housing 4. The electrical connector(s) 48 may also connect the second light source 22 to the control circuitry or components used to actuate the hand-held device 2 and trigger the light.

In an alternative to the embodiment of FIGS. 2 and 3, rather than the second heat sink 26 being in contact with the first heat sink 18 when the second treatment head portion 20 is attached to the main housing 4, the second heat sink 26 can be thermally coupled to the cooling unit 19 via a respective set of heat pipes. This second set of heat pipes can include one or more heat pipes, and this second set of heat pipes act to convey heat from the second heat sink 26 to the cooling unit heat sink 42. The fan 40 operates to pass air over the cooling unit heat sink 42 to cool the cooling unit heat sink 42 and thereby cool the hand-held device 2.

Some dimensions for some of the components in the hand-held device 2 of FIGS. 2 and 3 are provided below. These dimensions are exemplary and should not be considered limiting. All dimensions are presented in the form length×width×height. The first optical waveguide 16 can have dimensions 20×10×10 mm, the first light source 14 can have dimensions 20×10×1.5 mm, the first heat sink 18 can have dimensions 40×10×15 mm, each of the two second optical waveguide 24 parts in the second treatment head portion 20 can have dimensions 10×10×10 mm, each of the two second light source 22 parts can have dimensions 12×10×1.5 mm, each of the two second heat sink 26 parts can have dimensions 12×10×15 mm, each heat pipe 44 can have a 6 mm outside diameter, the cooling unit heat sink 42 can have dimensions 60×60×12 mm, and the fan 40 can have dimensions 60×60×20 mm.

Figure 4:
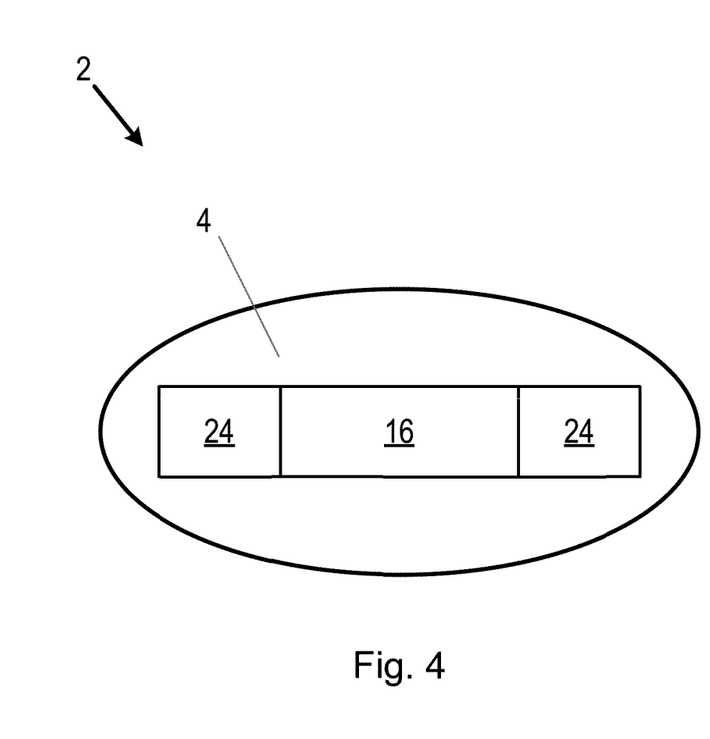
FIG. 4 is a front view showing a combination of a first treatment head portion and a second treatment head portion according to the embodiment in FIG. 2.

FIG. 4 is a front view of the hand-held device 2 of FIGS. 2 and 3 showing the hand-held device 2 in the second configuration in which the second treatment head portion 20 is coupled to the main housing 4. Thus, the two parts of the second optical waveguide 24 are positioned either side of the first optical waveguide 16, and the second treatment head portion 20 extends the size of the overall skin portion to be treated by the hand-held device 2 in two directions.

Figure 5:
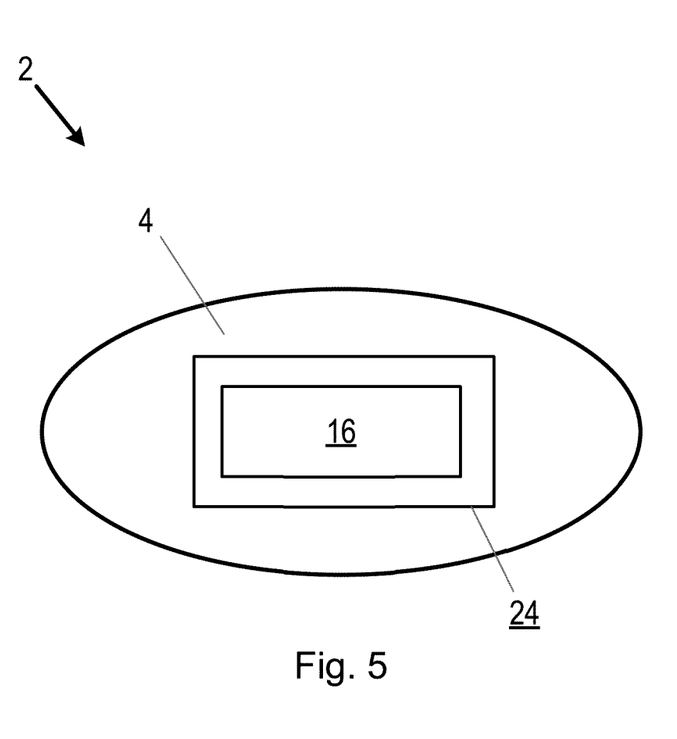
FIG. 5 is a front view showing a combination of a first treatment head portion and a second treatment head portion according to an alternative embodiment.

FIG. 5 is a front view of an alternative hand-held device 2 based on the hand-held device 2 of FIGS. 2 and 3. In this embodiment, the second treatment head portion 20 extends the size of the skin portion to be treated in all directions around the first treatment head portion 12 in the second configuration. Thus, the second light source 22, the second optical waveguide 24 and the second heat sink 26 are shaped so that they surround the first light source 14, the first optical waveguide 16 and the first heat sink 18.

It will be appreciated that multiple different second treatment head portions 20 can be provided for a particular hand-held device 2, with each second treatment head portion 20 providing a different overall skin treatment area size when coupled to the main housing 4. Thus, a user can select an appropriate second treatment head portion 20 for the size of the skin area to be treated, and this second treatment head portion 20 can be coupled to the main housing 4.

Figure 6:
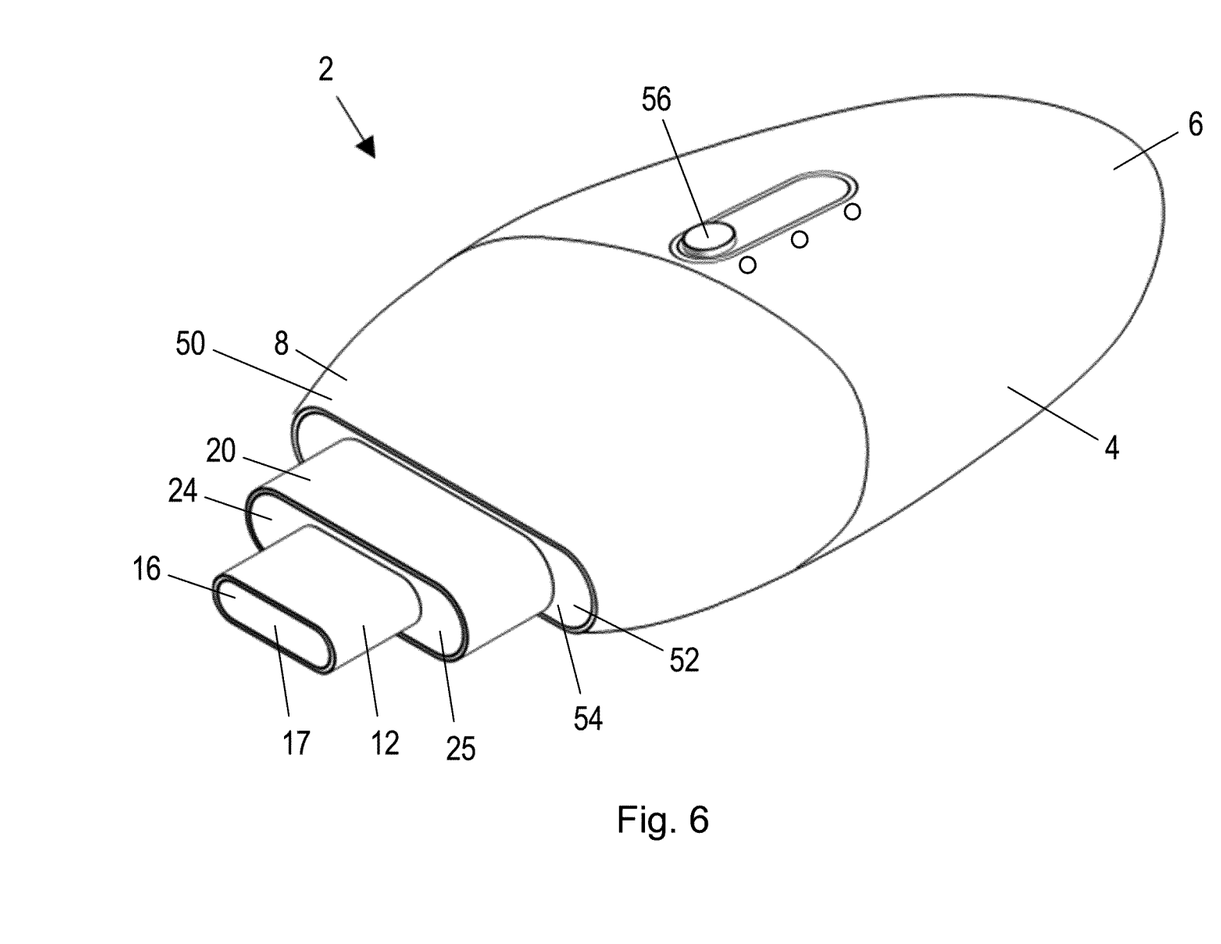
FIG. 6 is a perspective view of an exemplary hand-held device according to another embodiment.

FIG. 6 is a perspective view of an exemplary hand-held device according to another embodiment. In FIG. 6, components, features or elements of the hand-held device that are common to the embodiments shown in FIGS. 2 and 3 use the same reference numerals, and, unless otherwise indicated below, these components, features and elements are as described above with respect to FIGS. 2 and 3.

In the embodiment of FIG. 6, the hand-held device 2 is provided with a first treatment head portion 12, a second treatment head portion 20 and a third treatment head portion 50. The first treatment head portion 12 and the second treatment head portion 20 comprise the various components described above (i.e. light source, optical waveguide and heat sink), and the third treatment head portion 50 also includes a respective light source (referred to as a third light source), optical waveguide (third optical waveguide 52 having a third skin-contact surface 54) and heat sink (referred to as a third heat sink) in a similar arrangement to the components in the second treatment head portion 20. The three treatment head portions provide the hand-held device 2 with three configurations, to enable three different sized areas of skin to be treated with each light pulse. In the first configuration only the first treatment head portion 12 is used to treat skin, in the second configuration only the first treatment head portion 12 and the second treatment head portion 20 are used to treat skin thereby treating a larger area of skin than in the first configuration, and in the third configuration all of the first treatment head portion 12, the second treatment head portion 20 and the third treatment head portion 50 are used to treat skin, thereby treating a larger area of skin than in the second configuration.

In this embodiment, rather than the second treatment head portion 20 (or third treatment head portion 50) being removable from the main housing 4, two or more of the treatment head portions are moveable relative to each other and the other treatment head portion in order to set the different configurations. In the embodiment of FIG. 6, the third treatment head portion 50 is fixed to the main housing 4 (i.e. it cannot move relative to the main housing 4), and the first treatment head portion 12 and second treatment head portion 20 are movable relative to the third treatment head portion 50 and moveable relative to each other. The different configurations of the treatment head portions (corresponding to respective spatial arrangements of the first treatment head portion 12, the second treatment head portion 20 and the third treatment head portion 50) can be achieved by the treatment head portions being in a telescoping arrangement, with the first configuration corresponding to the arrangement being fully extended, the third configuration corresponding to the arrangement being fully retracted, and the second configuration corresponding to the arrangement where the first treatment head portion 12 and the second treatment head portion 20 are extended the same amount.

Thus, to set the hand-held device 2 in the first configuration, the first treatment head portion 12 is extended from the main housing 4 and also extended relative to both the second treatment head portion 20 and the third treatment head portion 50 (FIG. 6 shows the hand-held device 2 in this first configuration). In this configuration only the first skin-contact surface 17 of the first optical waveguide 16 is arranged in a treatment position relative to the main housing 4 so as to be able to contact skin over the first total surface area (when the main housing 4 is in an operational position relative to the skin), and only the first light source 14 is used to generate light.

To set the hand-held device 2 in the second configuration, the first treatment head portion 12 and the second treatment head portion 20 are extended from the main housing 4 and from the third treatment head portion 50 by the same amount. This configuration can be achieved by retracting the first treatment head portion 12 from the first configuration or extending the first treatment head portion 12 and second treatment head portion 20 from the main housing 4. In this configuration only the first skin-contact surface 17 of the first optical waveguide 16 and the second skin-contact surface 25 of the second optical waveguide 24 are arranged in a treatment position relative to the main housing 4 so as to be able to contact skin over the first total surface area and the second total surface area (when the main housing 4 is in an operational position relative to the skin), and only the first light source 14 and the second light source 22 are used to generate light.

To set the hand-held device 2 in the third configuration, the first treatment head portion 12 and the second treatment head portion 20 are retracted so that they are level with the third treatment head portion 50. In this configuration each of the first skin-contact surface 17 of the first optical waveguide 16, the second skin-contact surface 25 of the second optical waveguide 24 and the third skin-contact surface 54 of the third optical waveguide 52 are arranged in a treatment position relative to the main housing 4 so as to be able to contact skin, and all of the first light source 14, the second light source 22 and the third light source are used to generate light.

It will be appreciated that various mechanisms or controls can be provided to enable the hand-held device 2 to be set into the required configuration. In FIG. 6, a switch 56 is shown on the main housing 4 that can be actuated by the user and that moves the treatment head portions to the required configuration based on the position of the switch 56. The movement of the treatment head portions may be manual in response to the movement of the switch 56, for example the switch 56 can be mechanically linked to the treatment head portions so that the movement of the switch 56 correspondingly moves the treatment head portions. Alternatively, the treatment head portions may be moveable by a motor or other electronic means in response to movement of the switch 56.

As with the embodiments in FIGS. 2 and 3, the treatment head portions that are active in a particular configuration will be thermally coupled to the cooling unit in the main housing 4 so that the active light sources are cooled during use.

It will be appreciated that although the embodiment of FIG. 6 includes three treatment head portions, the way in which the treatment head portions are arranged and moveable to set the different configurations (and thus the different spatial arrangements) can also be applied to hand-held devices 2 having just two treatment head portions (e.g. as shown in FIGS. 1-3). Thus the first treatment head portion 12 in FIGS. 2 and 3 could be configured to be extended relative to the second treatment head portion 20 to enable the first configuration and retracted to enable the second configuration (or alternatively the second treatment head portion 20 could be retracted relative to the first treatment head portion 12 to enable the first configuration and the second treatment head portion 20 extended to enable the second configuration).

It will also be appreciated that rather than the third treatment head portion 50 being fixed to the main housing 4 and the other two treatment head portions being moveable relative thereto, the first treatment head portion 12 could be fixed relative to the main housing 4, and the second treatment head portion 20 and the third treatment head portion 50 can be retracted into or towards the main housing 4 to set the first configuration, and the second treatment head portion 20 and the third treatment head portion 50 can be extended from the main housing 4 to set the third configuration.

In a variation of the embodiment of FIG. 6, a hand-held device 2 can be provided with a first treatment head portion 12, a second treatment head portion 20 and a third treatment head portion 50, and in one configuration of the hand-held device 2 the first treatment head portion 12 can be used alone, in another configuration the second treatment head portion 20 can be used in combination with the first treatment head portion 12 while the third treatment head portion 50 is not used, and in another configuration the third treatment head portion 50 can be used in combination with the first treatment head portion 12 while the second treatment head portion 20 is not used. This arrangement of the hand-held device 2 can be useful where the configurations that use the second treatment head portion 20 and the third treatment head portion 50 respectively provide treatment for different sized and/or different shaped areas of skin. Of course, a fourth configuration may also be possible where the first treatment head portion 12, the second treatment head portion 20 and the third treatment head portion 50 are used together to treat the skin. This type of hand-held device 2 may be realised using an arrangement similar to that shown in FIGS. 1-3 (e.g. where the third treatment head portion 50 can be attached to the body 4 instead of the second treatment head portion 20), or realised using an arrangement similar to that shown in FIG. 6 (i.e. where two or more of the treatment head portions are moveable with respect to each other).

Figure 7:
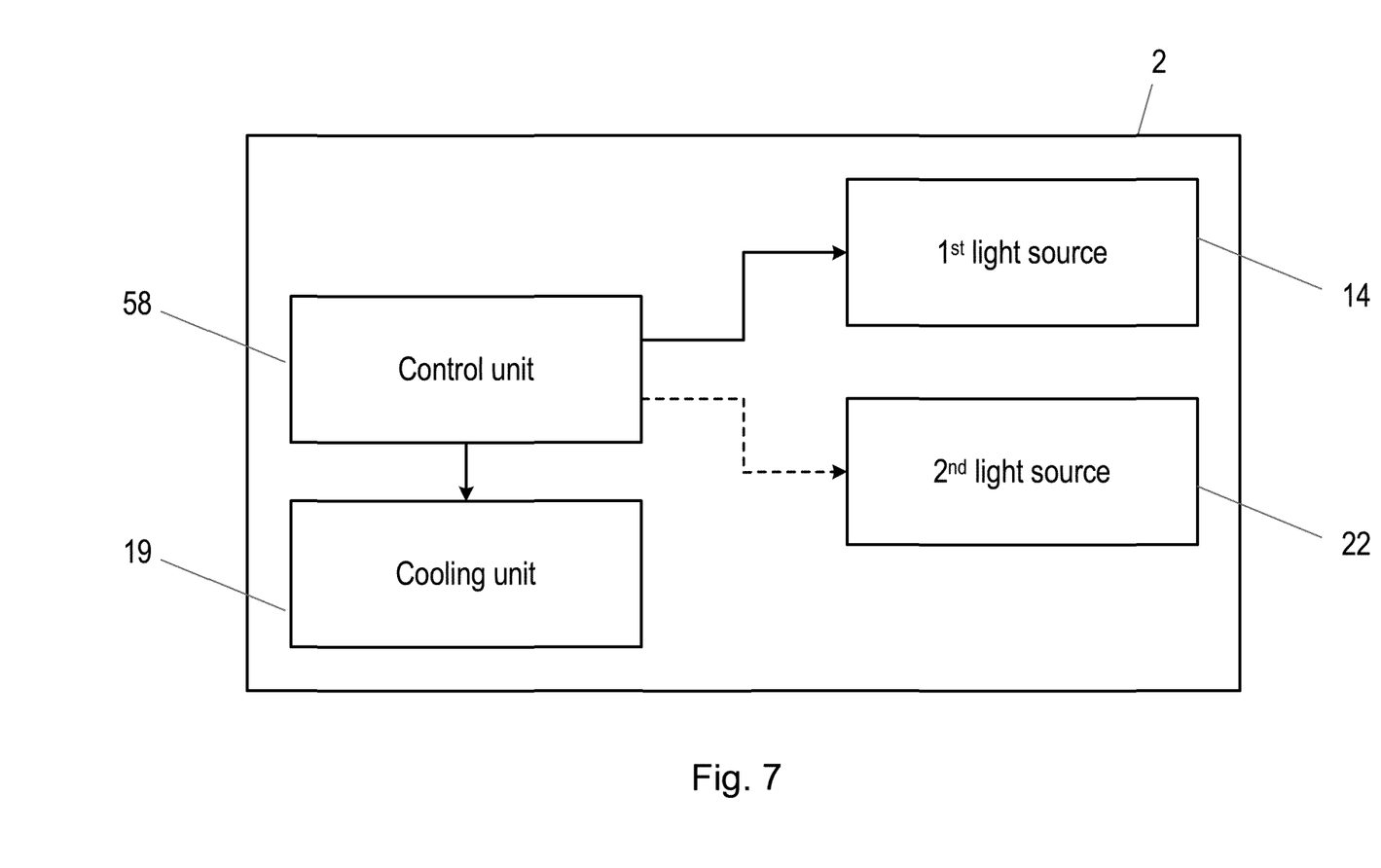
FIG. 7 is a block diagram illustrating components of a hand-held device according to various embodiments.

FIG. 7 is a block diagram illustrating components of a hand-held device 2 according to various embodiments. The hand-held device 2 comprises a first light source 14, a cooling unit 19 and a control unit 58. The control unit 58 is connected to the first light source 14 and the cooling unit 19. A second light source 22 is also shown, but the connection to the control unit 58 is shown with a dashed line representing that the second light source 22 (in the second treatment head portion 20) can be removed from the hand-held device 2 in some embodiments.

The control unit 58 controls the operation of the hand-held device 2. For example, in response to a trigger from the user of the hand-held device 2 (e.g. pressing a button, pulling a trigger, etc.) the control unit 58 controls the first light source 14, and the second light source 22 if required by the current configuration of the hand-held device 2, to generate light and perform the treatment operation on the skin of the subject. The control unit 58 also controls the cooling unit 19 to operate to cool the first light source 14 and the second light source 22 (if required). The control unit 58 can be implemented in numerous ways, with software and/or hardware, to perform the various functions described herein. The control unit 58 may comprise one or more microprocessors or digital signal processor (DSPs) that may be programmed using software or computer program code to perform the required functions and/or to control components of the control unit 58 to effect the required functions. The control unit 58 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The control unit 58 is connected to a memory unit (not shown in FIG. 7) that can store data, information and/or signals for use by the control unit 58 in controlling the operation of the hand-held device 2. In some implementations the memory unit stores computer-readable code that can be executed by the control unit 58 so that the control unit 58 performs one or more required functions. The memory unit can comprise any type of non-transitory machine-readable medium, such as cache or system memory including volatile and non-volatile computer memory such as random access memory (RAM) static RAM (SRAM), dynamic RAM (DRAM), read-only memory (ROM), programmable ROM (PROM), erasable PROM (EPROM) and electrically erasable PROM (EEPROM), implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

It will be appreciated that a practical implementation of a hand-held device 2 may include additional components to those shown in FIG. 7 and the earlier figures. For example the hand-held device 2 may also include a power supply, such as a battery, or components for enabling the hand-held device 2 to be connected to a mains power supply.

There is therefore provided an improved hand-held device that can be adapted to treat different sized areas of skin.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A hand-held device for applying light to skin of a subject to perform a skin treatment operation, the hand-held device comprising:
 a rigid main housing accommodating a cooling unit;
 a first treatment head portion coupled to the main housing for performing the skin treatment operation on a first skin portion, wherein the first treatment head portion comprises a first optical waveguide having a first skin-contact surface with a first total surface area, a first light source for generating light and applying the light to the first skin portion via the first optical waveguide and the first skin-contact surface, and a first heat sink thermally coupled to the first light source and to the cooling unit;
 a second treatment head portion for performing the skin treatment operation on a second skin portion adjacent to the first skin portion, wherein the second treatment head portion comprises a second optical waveguide having a second skin-contact surface with a second total surface area, a second light source for generating light and applying the light to the second skin portion via the second optical waveguide and the second skin-contact surface, and a second heat sink thermally coupled to the second light source;
 wherein the hand-held device is operable in
 (i) a first configuration in which the first and second treatment head portions are in a first spatial arrangement relative to the main housing such that, in an operational position of the main housing relative to the skin, only the first skin-contact surface is arranged in a treatment position relative to the main housing such as to be able to contact the skin over the first total surface area; and
 (ii) a second configuration in which the second treatment head portion is coupled to the main housing and the second heat sink is thermally coupled to the cooling unit, and in which the first and second treatment head portions are in a second spatial arrangement relative to the main housing, different from the first spatial arrangement, such that, in the operational position of the main housing, the first skin-contact surface and the second skin-contact surface are each arranged in a treatment position relative to the main housing such as to be able to contact the skin over, respectively, the first total surface area and the second total surface area, and wherein the second light source and the second optical waveguide are configured to surround the first light source and the first optical waveguide in the second configuration.

2. The hand-held device as claimed in claim 1, wherein the second treatment head portion is configured to be detachable or removable from the hand-held device, and wherein the second treatment head portion is detached or removed from the hand-held device to provide the first spatial arrangement in the first configuration and the second treatment head portion is attached to the hand-held device to provide the second spatial arrangement in the second configuration.

3. The hand-held device as claimed in claim 2, wherein the second treatment head portion is configured to be detachable or removable from the first treatment head portion, and wherein the second treatment head portion is detached or removed from the first treatment head portion to provide the first spatial arrangement in the first configuration and the second treatment head portion is attached to the first treatment head portion to provide the second spatial arrangement in the second configuration.

4. The hand-held device as claimed in claim 1, wherein in the second configuration the second heat sink is thermally coupled to the cooling unit via the first heat sink.

5. The hand-held device as claimed in claim 1, wherein the first heat sink is thermally coupled to the cooling unit via a first set of heat pipes, and wherein, in the second configuration, the second heat sink is thermally coupled to the cooling unit via a second set of heat pipes.

6. The hand-held device as claimed in claim 1, wherein the cooling unit comprises a cooling unit heat sink and a fan.

7. The hand-held device as claimed in claim 6, wherein the first heat sink is thermally coupled to the cooling unit heat sink.

8. The hand-held device as claimed in claim 1, wherein, in the second configuration the second optical waveguide is adjacent to the first optical waveguide such that the first skin portion and the second skin portion are a substantially continuous skin region.

9. The hand-held device as claimed in claim 1, wherein the second heat sink is configured to surround the first heat sink in the second configuration.

10. A hand-held device for applying light to skin of a subject to perform a skin treatment operation, the hand-held device comprising:
 a rigid main housing accommodating a cooling unit;
 a first treatment head portion coupled to the main housing for performing the skin treatment operation on a first skin portion, wherein the first treatment head portion comprises a first optical waveguide having a first skin-contact surface with a first total surface area, a first light source for generating light and applying the light to the first skin portion via the first optical waveguide and the first skin-contact surface, and a first heat sink thermally coupled to the first light source and to the cooling unit;
 a second treatment head portion for performing the skin treatment operation on a second skin portion adjacent to the first skin portion, wherein the second treatment head portion comprises a second optical waveguide having a second skin-contact surface with a second total surface area, a second light source for generating light and applying the light to the second skin portion via the second optical waveguide and the second skin-contact surface, and a second heat sink thermally coupled to the second light source; and a treatment head protective cover configured to be detachable or removable from the hand-held device, wherein the hand-held device is operable in
(i) a first configuration in which the first and second treatment head portions are in a first spatial arrangement relative to the main housing such that, in an operational position of the main housing relative to the skin, only the first skin-contact surface is arranged in a treatment position relative to the main housing such as to be able to contact the skin over the first total surface area; and
(ii) a second configuration in which the second treatment head portion is coupled to the main housing and the second heat sink is thermally coupled to the cooling unit, and in which the first and second treatment head portions are in a second spatial arrangement relative to the main housing, different from the first spatial arrangement, such that, in the operational position of the main housing, the first skin-contact surface and the second skin-contact surface are each arranged in a treatment position relative to the main housing such as to be able to contact the skin over, respectively, the first total surface area and the second total surface area, wherein the second treatment head portion is detached or removed from at least one of the first treatment head portion or the hand-held device to provide the first spatial arrangement in the first configuration, wherein the second treatment head portion is attached to the at least one of the first treatment head portion or the hand-held device to provide the second spatial arrangement in the second configuration, and wherein the treatment head protective cover is attached to the hand-held device in the first configuration, and detached or removed from the hand-held device in the second configuration.

11. A hand-held device for applying light to skin of a subject to perform a skin treatment operation, the hand-held device comprising:

a rigid main housing accommodating a cooling unit;

a first treatment head portion coupled to the main housing for performing the skin treatment operation on a first skin portion, wherein the first treatment head portion comprises a first optical waveguide having a first skin-contact surface with a first total surface area, a first light source for generating light and applying the light to the first skin portion via the first optical waveguide and the first skin-contact surface, and a first heat sink thermally coupled to the first light source and to the cooling unit;

a second treatment head portion for performing the skin treatment operation on a second skin portion adjacent to the first skin portion, wherein the second treatment head portion comprises a second optical waveguide having a second skin-contact surface with a second total surface area, a second light source for generating light and applying the light to the second skin portion via the second optical waveguide and the second skin-contact surface, and a second heat sink thermally coupled to the second light source;

wherein the hand-held device is operable in
(i) a first configuration in which the first and second treatment head portions are in a first spatial arrangement relative to the main housing such that, in an operational position of the main housing relative to the skin, only the first skin-contact surface is arranged in a treatment position relative to the main housing such as to be able to contact the skin over the first total surface area; and
(ii) a second configuration in which the second treatment head portion is coupled to the main housing and the second heat sink is thermally coupled to the cooling unit, and in which the first and second treatment head portions are in a second spatial arrangement relative to the main housing, different from the first spatial arrangement, such that, in the operational position of the main housing, the first skin-contact surface and the second skin-contact surface are each arranged in a treatment position relative to the main housing such as to be able to contact the skin over, respectively, the first total surface area and the second total surface area, and wherein the first treatment head portion is moveably coupled to the main housing, and is moveable between an extended position in the first configuration in which the first skin-contact surface of the first treatment head portion extends from the main housing beyond the second skin-contact surface of the second treatment head portion, and a retracted position in the second configuration in which the first skin-contact surface of the first optical waveguide is adjacent to the second skin-contact surface of the second optical waveguide.

12. The hand-held device as claimed in claim 11, wherein the second treatment head portion is in a fixed position with respect to the main housing.

13. The hand-held device as claimed in claim 11, wherein the first heat sink is thermally coupled to the cooling unit via a first set of heat pipes, and wherein, in the second configuration, the second heat sink is thermally coupled to the cooling unit via a second set of heat pipes.

14. The hand-held device as claimed in claim 11, wherein the cooling unit comprises a cooling unit heat sink and a fan, wherein the first heat sink is thermally coupled to the cooling unit heat sink.

15. The hand-held device as claimed in claim 11, wherein, in the second configuration the second optical waveguide is adjacent to the first optical waveguide such that the first skin portion and the second skin portion are a substantially continuous skin region.

16. A hand-held device for applying light to skin of a subject to perform a skin treatment operation, the hand-held device comprising:

a rigid main housing accommodating a cooling unit;

a first treatment head portion coupled to the main housing for performing the skin treatment operation on a first skin portion, wherein the first treatment head portion comprises a first optical waveguide having a first skin-contact surface with a first total surface area, a first light source for generating light and applying the light to the first skin portion via the first optical waveguide and the first skin-contact surface, and a first heat sink thermally coupled to the first light source and to the cooling unit;

a second treatment head portion for performing the skin treatment operation on a second skin portion adjacent to the first skin portion, wherein the second treatment head portion comprises a second optical waveguide having a second skin-contact surface with a second total surface area, a second light source for generating light and applying the light to the second skin portion via the second optical waveguide and the second skin-contact surface, and a second heat sink thermally coupled to the second light source;

wherein the hand-held device is operable in
(i) a first configuration in which the first and second treatment head portions are in a first spatial arrangement relative to the main housing such that, in an operational position of the main housing relative to the skin, only the first skin-contact surface is arranged in a treatment position relative to the main housing such as to be able to contact the skin over the first total surface area; and
(ii) a second configuration in which the second treatment head portion is coupled to the main housing and the second heat sink is thermally coupled to the cooling unit, and in which the first and second treatment head portions are in a second spatial arrangement relative to the main housing, different from the first spatial arrangement, such that, in the operational position of the main housing, the first skin-contact surface and the second skin-contact surface are each arranged in a treatment position relative to the main housing such as to be able to contact the skin over, respectively, the first total surface area and the second total surface area, and
wherein the second treatment head portion is moveably coupled to the main housing, and is moveable between a retracted position in the first configuration in which the first skin-contact surface of the first treatment head portion extends from the main housing beyond the second skin-contact surface of the second treatment head portion, and an extended position in the second configuration in which the first skin-contact surface of the first optical waveguide is adjacent to the second skin-contact surface of the second optical waveguide.

17. The hand-held device as claimed in claim 16, wherein the first treatment head portion is in a fixed position with respect to the main housing.

18. The hand-held device as claimed in claim 16, wherein the first heat sink is thermally coupled to the cooling unit via a first set of heat pipes, and wherein, in the second configuration, the second heat sink is thermally coupled to the cooling unit via a second set of heat pipes.

19. The hand-held device as claimed in claim 16, wherein the cooling unit comprises a cooling unit heat sink and a fan, wherein the first heat sink is thermally coupled to the cooling unit heat sink.

20. The hand-held device as claimed in claim 16, wherein, in the second configuration the second optical waveguide is adjacent to the first optical waveguide such that the first skin portion and the second skin portion are a substantially continuous skin region.

* * * * *